United States Patent
Hennings et al.

(10) Patent No.: US 10,791,955 B2
(45) Date of Patent: Oct. 6, 2020

(54) ASSESSMENT OF NERVE FIBER EXCITABILITY

(71) Applicant: AALBORG UNIVERSITET, Aalborg Øst (DK)

(72) Inventors: Kristian Hennings, Aalborg Sv (DK); Carsten Dahl Mørch, Aalborg (DK); Ole Kæseler Andersen, Skørping (DK); Lars Arendt-Nielsen, Aalborg (DK)

(73) Assignee: AALBORG UNIVERSITET, Aalborg Øst (DK)

( * ) Notice: Subject to any disclaimer, the term of this patent is extended or adjusted under 35 U.S.C. 154(b) by 510 days.

(21) Appl. No.: 15/558,759

(22) PCT Filed: Mar. 17, 2016

(86) PCT No.: PCT/EP2016/055826
§ 371 (c)(1),
(2) Date: Sep. 15, 2017

(87) PCT Pub. No.: WO2016/146758
PCT Pub. Date: Sep. 22, 2016

(65) Prior Publication Data
US 2018/0064362 A1    Mar. 8, 2018

(30) Foreign Application Priority Data

Mar. 19, 2015 (SE) ....................... 1550330

(51) Int. Cl.
*A61B 5/0488* (2006.01)
*A61B 5/0484* (2006.01)
(Continued)

(52) U.S. Cl.
CPC .......... *A61B 5/0488* (2013.01); *A61B 5/4052* (2013.01); *A61N 1/0456* (2013.01); *A61B 5/0484* (2013.01); *A61N 1/36034* (2017.08)

(58) Field of Classification Search
CPC ... A61B 5/0488; A61B 5/4052; A61B 5/0484; A61N 1/0456; A61N 1/36014
(Continued)

(56) References Cited

U.S. PATENT DOCUMENTS 7,089,059 B1    8/2006  Pless
2014/0148725 A1    5/2014  Cadwell
(Continued)

OTHER PUBLICATIONS

Hennings, K., et al., "Orderly Activation of Human Motor Neurons Using Electrical Ramp Prepulses," Clinical Neurophysiology, 116(3):597-604, Mar. 2005. (Year: 2005).*
(Continued)

*Primary Examiner* — Navin Natnithithadha
(74) *Attorney, Agent, or Firm* — Christenson O'Connor Johnson Kindness PLLC

(57) ABSTRACT

A method for assessing nerve fiber excitability is disclosed. The method comprises: arranging an electrode in contact with skin of a person; determining a first and a second threshold value based on a stimulation current pulse of a first and a second waveform, respectively; wherein said determining of the first threshold value and said determining of the second threshold value each comprises: repeatedly providing a stimulation current pulse of the first or second waveform, respectively, through the electrode, wherein a stimulation current strength is altered between repetitions; and receiving signals from an interaction element with which the person interacts, said signals from the interaction element providing an indication of the first threshold value or the second threshold value, respectively, corresponding to a stimulation current strength necessary to be perceived by
(Continued)

the person; and determining at least one measure of psychophysical perception based on the determined first and second threshold values.

24 Claims, 3 Drawing Sheets

(51) Int. Cl.
    *A61B 5/00*     (2006.01)
    *A61N 1/04*     (2006.01)
    *A61N 1/36*     (2006.01)

(58) Field of Classification Search
    USPC .......................................................... 600/546
    See application file for complete search history.

(56) References Cited

U.S. PATENT DOCUMENTS

2014/0303682 A1* 10/2014 Siff .................... A61N 1/36021
    607/41
2015/0257970 A1* 9/2015 Mucke ................. A61N 1/0476
    601/21

OTHER PUBLICATIONS

International Search Report dated Jun. 2, 2016, issued in corresponding International Application No. PCT/EP2016/055826, filed Mar. 17, 2016, 7 pages.

Bostock, H., et al., "Threshold Tracking Techniques in the Study of Human Peripheral Nerve," Muscle & Nerve 21(2):137-158, Feb. 1998.

Friedli, W.G., and M. Meyer, "Strength-Duration Curve: A Measure for Assessing Sensory Deficit in Peripheral Neuropathy," Journal of Neorology, Neurosurgery, and Psychiatry 47(2):184-189, Feb. 1984.

Hennings, K., et al., "Orderly Activation of Human Motor Neurons Using Electrical Ramp Prepulses," Clinical Neurophysiology 116(3):597-604, Mar. 2005.

Hennings, K., et al., "Selective Activation of Small-Diameter Motor Fibres Using Exponentially Rising Waveforms: A Theoretical Study," Medical and Biological Engineering and Computing 43(4):493-500, Aug. 2005.

Keller, T., et al., "Transcutaneous Functional Electrical Stimulator 'Compex Motion,'" Artificial Organs 26(3):219-223, Mar. 2002.

\* cited by examiner

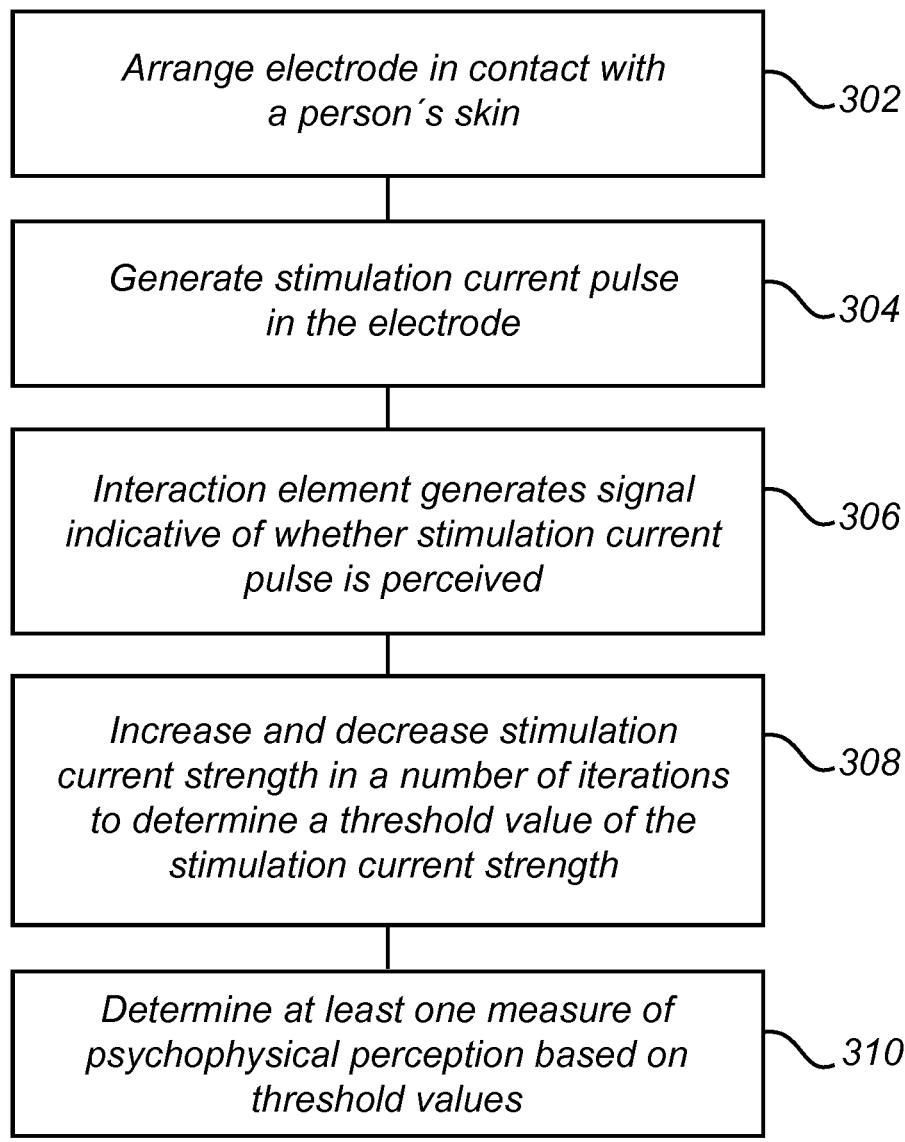

```
┌─────────────────────────────────┐
│  Arrange electrode in contact with │──302
│       a person's skin           │
└─────────────────────────────────┘
                │
┌─────────────────────────────────┐
│  Generate stimulation current pulse │──304
│        in the electrode         │
└─────────────────────────────────┘
                │
┌─────────────────────────────────┐
│  Interaction element generates signal │
│  indicative of whether stimulation current │──306
│        pulse is perceived       │
└─────────────────────────────────┘
                │
┌─────────────────────────────────┐
│  Increase and decrease stimulation │
│  current strength in a number of iterations │──308
│  to determine a threshold value of the │
│    stimulation current strength │
└─────────────────────────────────┘
                │
┌─────────────────────────────────┐
│  Determine at least one measure of │
│  psychophysical perception based on │──310
│        threshold values         │
└─────────────────────────────────┘
```

*Fig. 3*

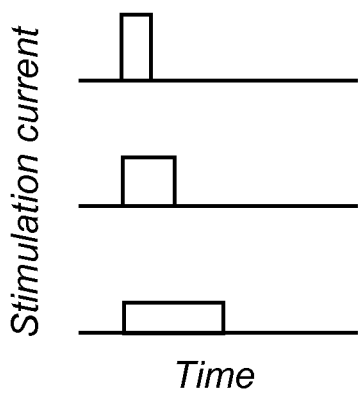

*Fig. 4a*

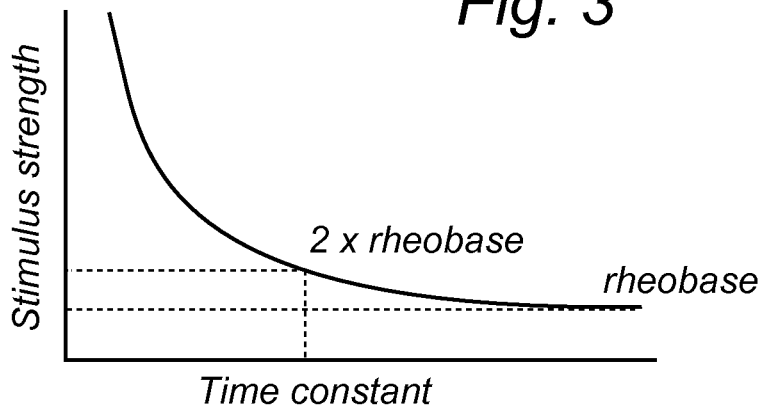

*Fig. 4b*

ASSESSMENT OF NERVE FIBER EXCITABILITY

TECHNICAL FIELD

The invention disclosed generally relates to determining a response to a stimulation of nerve fibers of a patient. In particular, the invention relates to a method and a system for assessment of nerve fiber excitability, and a control unit used in such a method.

BACKGROUND

Peripheral neuropathy is a condition, in which a large part of the peripheral nervous system or single peripheral nerves have been damaged. The condition causes suffering and disability for many patients and as the condition progresses it may cause chronic constant or cold evoked pain.

Peripheral neuropathy may have several causes. For instance, small fiber neuropathy is frequent among many conditions, e.g. postherpetic neuralgia, impaired glucose intolerance, connective tissue disease, and diabetes mellitus. Peripheral neuropathy may also occur as a side effect of chemotherapy.

The nervous system comprises several types of nerves, which are adapted to transmit signals relating to different conditions. Afferent nerves transmit signals relating to external sensations. There are also several types of afferent nerves, including Aβ-fibers that are thick and may transmit signals in response to pressure or vibration, and Aδ-fibers that are thin and transmit fast signals relating to pain, temperature or pressure. Peripheral neuropathy may often affect the thick Aβ-fibers first. However, in other situations, e.g. as a side effect to some treatments with chemotherapy, nociceptors, such as Aδ-fibers or C-fibers, may be affected first.

Neuropathic pain is a clinical challenge regarding both diagnosis and treatment. The best remedy is often to avoid further progression in nerve degeneration. In this regard, it would be advantageous to enable early diagnosis of neuropathy in order to enable at least slowing down of nerve degeneration at an early stage.

There are existing methods for providing tests of nerve functions. Commonly used methods are different types of nerve conduction studies, wherein an electrode is arranged on the skin over a nerve and an electrical pulse is provided to stimulate the nerve. Nerve conduction studies that assess latency and amplitude of a compound action potential of peripheral nerves quantify the loss of myelination and loss of nerve fibers.

Similarly, Bostock H, Cikurel K, Burke D, "Threshold tracking techniques in the study of human peripheral nerve", Muscle & Nerve 21: 137-158, 1998, discloses threshold tracking as an electrophysiological test of nerve function. Threshold tracking tests nerve excitability, which depends on membrane properties of axons at a site of stimulation. These are studied by measuring the excitability of the nerve fibers while they are subject to a series of conditioning stimuli.

However, both nerve conduction studies and the threshold tracking method require direct measurements of nerve activity in that it requires an electrode to physically measure the signal transmitted in the nerve fiber. Further, it may be difficult to perform in that the electrodes have to be located precisely onto either a sensory or a motor nerve, and the electrical stimulations are powerful and can be painful to the patient. Furthermore, the electrical stimulation provided by the electrodes first activates the large Aβ-fibers. Therefore, the methods do not provide any insight to nerve fiber excitability of nociceptors, because the nociceptor activity cannot be recorded by the direct measurement.

With regard to assessment of nerve fiber excitability of nociceptors, quantitative sensory testing is a known method. Quantitative sensory testing consists of different methods to test heat and mechanical, nociceptive and non-nociceptive stimuli and receiving a subjective assessment of perception from the patient. This type of method only provides measures of the presence of the nerve fibers but may not provide insight to the properties of the nerve fiber membrane.

SUMMARY OF THE INVENTION

It is an object of the invention to enable a method that may provide assessment of nerve fiber excitability in a way that is at least relatively painless to the patient. It is a particular object of the invention to enable assessment of nerve fiber excitability in a repeatable manner without requiring any direct measurements of nerve activity. It is another object of the invention to enable a method that is suitable for assessment of the nociceptors.

These and other objects of the invention are at least partly met by the invention as defined in the independent claims. Preferred embodiments are set out in the dependent claims.

According to a first aspect of the invention, there is provided a method for assessment of nerve fiber excitability, said method comprising: arranging an electrode in contact with skin of a person; determining a first threshold value based on a stimulation current pulse of a first waveform; determining a second threshold value based on a stimulation current pulse of a second waveform different from the first waveform, wherein said determining of the first threshold value and said determining of the second threshold value each comprises: repeatedly providing a stimulation current pulse of the first or second waveform, respectively, through the electrode, wherein a stimulation current strength of the stimulation current pulse is altered between repetitions; and receiving signals from an interaction element with which the person interacts, said signals from the interaction element providing an indication of the first threshold value or the second threshold value, respectively, of a stimulation current strength of the stimulation current pulse, the first and second threshold value, respectively, corresponding to a stimulation current strength necessary to trigger a sufficiently large nerve fiber excitation such that it is perceived by the person; and determining at least one measure of psychophysical perception based on the determined first and second threshold values.

According to a second aspect of the invention, there is provided a control unit for use in assessment of nerve fiber excitability, wherein said control unit is configured to control a stimulation current strength of a stimulation current pulse in an electrode and a waveform for the stimulation current pulse, said control unit being configured to cause a first and a second stimulation sequence using a first waveform and a second waveform different from the first waveform, respectively, wherein said control unit is arranged to receive a signal from an interaction element with which a person interacts for providing an indication whether the stimulation current pulse has triggered a sufficiently large nerve fiber excitation such that it is perceived by the person, and wherein said control unit comprises a processing unit, which is arranged to, within each of the first and the second simulation sequences: determine whether a stimulation current strength to be used in a next stimulation current pulse is to be increased or decreased based on said received signal from the interaction element; store an association of values of stimulation current strength to received signals from the interaction element indicating that the stimulation current pulse is perceived by the person; determine a threshold value of the stimulation current strength based on the stored association; and said processing unit being further arranged to determine at least one measure of psychophysical perception based on a first threshold value determined for the first simulation sequence and a second threshold value determined for the second simulation sequence.

According to a third aspect of the invention, there is provided a system for assessment of nerve fiber excitability, said system comprising: a control unit according to the second aspect of the invention; an electrode, which is adapted to be arranged in contact with skin of a person, wherein the electrode is operatively connected to the control unit for control of a stimulation current pulse in the electrode; and an interaction element, which is arranged to record an interaction of the person with the interaction element providing an indication whether the stimulation current pulse has triggered a sufficiently large nerve fiber excitation such that it is perceived by the person, said interaction element being further arranged to transmit a signal to the control unit based on the interaction of the person.

Thanks to the invention, a measure of a psychophysical perception may be determined. This measure may then be used for a number of different purposes. For instance, the measure may form the basis for diagnosing a condition of the patient or determining progress of degeneration of nerve fibers of the patient and/or for evaluating medications, such as the effect of anaesthetic substances.

According to the invention, a subject that is exposed to the electrode stimulation is involved in the establishment of a first and a second threshold value. By involving the subject in the establishment of the at least one measure of psychophysical perception, the determined threshold values are perception-based and an apparent subjective element is introduced in the method. However, thanks to the invention determining a first and a second threshold value of stimulation current pulses having different waveforms, there is gathered information relating to different types of stimuli using the same subjective element. The different waveforms may stimulate the nerve fibers in different manners, providing separate measurements relating to signal propagation in nerve fibers. Hence, although the measurements involve input regarding perception provided by a patient, the determined first and second threshold values may be used for obtaining a quantitative measurement of nerve fiber excitability less prone to subjective bias.

According to the invention, a non-natural stimulus of nerve fibers is used, namely a stimulus based on an electrical current. It is an insight of the invention that even though a non-natural stimulus is used, the stimulus can excite nerve fibers to cause the stimulus to be perceived by a person. Further, by means of using stimulation current pulses having different waveforms, a response by the person relating to the perception of a stimulation current pulse can then be recorded and analyzed in order to determine at least one measure of psychophysical perception.

According to an embodiment, the method further comprises determining at least a third threshold value based on a stimulation current pulse of a third waveform different from the first and second waveforms, wherein said determining of the at least third threshold value is performed in the same manner as the determining of the first and second threshold values; and wherein said determining of at least one measure of psychophysical perception is further based on the determined at least third threshold value. Hence, measurements of a plurality of threshold values relating to a plurality of stimuli may be performed and the combination of determined threshold values may be used for establishing the at least one measure of psychophysical perception. The combination of a plurality of measurements promotes an objectiveness of the method.

In an embodiment, the arranging of an electrode in contact with skin of the person comprises using an array of small area electrodes having an area of less than 5 mm$^2$ such that small myelinated, afferent nerve fibers are preferentially stimulated by the stimulation current pulse. In an embodiment, the small area electrodes have an area in the range of 0.1-5 mm$^2$, which would be sufficient to preferentially stimulate small myelinated, afferent nerve fibers. In another embodiment, the small area electrodes have an area in the range of 0.2-1 mm$^2$.

Using an array of small electrodes, local high current densities may be formed in the surface of the skin of a subject, where pain sensing fibers are abundant. The stimulation current may thus preferentially activate the pain sensing fibers, and this type of electrode may therefore be used for preferentially stimulating nociceptors of a subject. The stimulation of nociceptors may cause a pricking or burning sensation, which may be perceived by the subject and, therefore, the subject may provide input as to a threshold of the stimulation current strength at which the stimulation pulse may be perceived. This implies that, according to the embodiment of the invention, it is possible to determine a measure of psychophysical perception related to the nociceptors. Such measure has previously not been possible to establish using non-invasive measurement technologies.

According to another embodiment, the arranging of an electrode in contact with skin of the person comprises using an electrode patch having an electrode area larger than 10 mm$^2$ such that large myelinated, afferent nerve fibers are stimulated by the stimulation current pulse. In an embodiment, the electrode patch has an electrode area in the range of 10-250 mm$^2$, which would be sufficient to preferentially stimulate large myelinated, afferent nerve fibers. In another embodiment, the electrode patch has an electrode area in the range of 50-200 mm$^2$.

Using a relatively large electrode patch, tactile nerve fibers may be selectively activated. This type of electrode may therefore be used for selectively stimulating Aβ-fibers of the subject. This implies that, according to the embodiment of the invention, it is possible to determine a measure of psychophysical perception related to the Aβ-fibers. Hence, a measure of psychophysical perception may be obtained without requiring invasive measurements of nerve signals in the body of the subject.

A plurality of different stimulation current pulses having different waveforms may be used and corresponding threshold values for the stimulation current strength necessary to trigger a perceivable nerve fiber excitation may be determined.

According to an embodiment, a waveform of one of the stimulation current pulses used is a square waveform having a constant stimulation current pulse during a defined length of time. Further, at least two different defined lengths of time of the stimulation current pulse are used and the determining of a threshold value comprises determining a duration-dependent threshold value of the stimulation current strength for each of the defined lengths of time of the waveform.

Thanks to the determining of at least two duration-dependent, perception-based threshold values of the stimulation current strength, a strength duration (SD) relation may be analyzed. SD is a property in a nerve describing how an activation threshold decreases as the duration of the square pulse stimulation is increased. The SD relation is a hyperbolic relationship that can be described by a time constant describing the decrease and a rheobase describing the threshold of an infinitely long pulse. Using the at least two measured, perception-based threshold values for different pulse durations, the time constant and the rheobase may be calculated. SD data may provide information about passive properties of a nodal membrane of a nerve and voltage gated sodium channels in the nodal membrane. Therefore, any pathology that affects passive properties of the membrane, such as demyelinization exposing more of an axon of the nerve, may also affect the SD relation and may be identified by means of the capturing of SD data.

According to an embodiment, a waveform of one of the stimulation current pulses used is a conditioning pulse with a strength insufficient of activation of nerve fibers and a following stimulation current pulse.

The conditioning pulse affects the threshold for the following stimulation current pulse, and this threshold change may be used in analysis of nerve fiber excitability.

In one embodiment, a conditioning pulse is used such that the conditioning pulse depolarizes a transmembrane potential of nerve fibers. In other words, the conditioning pulse is positive. This implies that the perception-based threshold value for the following stimulation current pulse is reduced.

In another embodiment, a conditioning pulse is used such that the conditioning pulse hyperpolarizes a transmembrane potential of nerve fibers. In other words, the conditioning pulse is negative. This implies that the perception-based threshold value for the following stimulation current pulse is increased (or negatively reduced).

According to an embodiment, durations of at least two different lengths of time of the conditioning pulse with an immediately following stimulation current pulse are used, and the determining of a threshold value comprises determining a duration-dependent threshold value of the stimulation current strength for each of the defined lengths of time of the conditioning pulse.

Determinations of the perception-based threshold value of the stimulation current pulse following a conditioning pulse may be compared to determinations of another perception-based threshold value, e.g. using a stimulation current pulse with a square waveform. A threshold value reduction may thus be analyzed. The threshold value reduction may be caused by potential differences across an internodal membrane potential. Further, for a longer depolarization pulse, the threshold value reduction is decreased, which may be caused by activation of slow potassium channels. For an increased duration of the hyperpolarizing conditioning pulse, the threshold value reduction is counteracted by a mechanism generated by activation of axonal inward rectifying channels. Hence, using conditioning pulses with different durations, further information about the nerve fiber excitability may be obtained.

According to an embodiment, durations of at least two different lengths of time between the conditioning pulse and the following stimulation current pulse are used, and the determining of a threshold value comprises determining a duration-dependent threshold value of the stimulation current strength for each of the defined lengths of time between the conditioning pulse and the following stimulation current pulse. For this type of stimulation current pulse, it is also possible to analyze the reduction of the perception-based threshold value caused by the conditioning pulse. The threshold value reduction may provide information of passive properties of a nodal membrane of a nerve and voltage gated sodium channels in the nodal membrane.

According to an embodiment, a waveform of one of the stimulation current pulses used defines a pulse comprising a leading edge, wherein the stimulation current is gradually increased to the stimulation current. A nerve fiber may accommodate to a gradually increasing stimulation current. Hence, using a relatively long stimulation current pulse, with a leading edge being longer than approximately 10 ms, an accommodation of the nerve fiber to the slowly increasing electrical stimulation may be observed. The accommodation of the nerve fiber to the gradually increasing stimulation current may be related to a proportion of persistent sodium channels in the nerve fibers. A larger proportion may lead to the nerve fibers being less responsive to accommodation. Hence, using this type of waveform, information about persistent sodium channels in the nerve fibers may be obtained.

According to an embodiment, the determining of the threshold values using respective waveforms of the stimulation current pulse each further comprises: controlling the stimulation current strength of the stimulation current pulse based on received signals from the interaction element.

This implies that the stimulation current strength provided through the electrode may be based on input from a person that is subject to the stimulation and that the stimulation current strength may thus be controlled between the repetitively provided stimulation current pulses such that a perception-based threshold value may be established.

According to an embodiment, the controlling of the stimulation current strength comprises changing the stimulation current strength up and down around a threshold value in a plurality of iterations, wherein the determining of a threshold value is based on the plurality of iterations. This implies that the person being subject to the stimulation is required to a plurality of times identify that the stimulation current strength is increased or decreased past a threshold value corresponding to a strength necessary to trigger a sufficiently large nerve fiber excitation such that it is perceived by the person. Hence, the threshold value may be accurately determined by being based on several identifications of the person.

In an embodiment, a size of difference in stimulation current strength between repetitions of stimulation current pulses is altered between the plurality of iterations. This implies that an approximate threshold value may first be determined by initially increasing the stimulation current strength in large steps. When the approximate threshold value is determined, successively smaller steps, i.e. sizes of the difference in stimulation current strength between repetitions, may be used in order to tune in on the threshold value. Other schemes of altering the size of difference in stimulation current strength between repetitions may be contemplated. For instance, the altering of the size may be made in a completely or partially random manner, such that the person may not anticipate the stimulation current strength to be used.

According to an embodiment, the method further comprises comparing the determined at least one measure of psychophysical perception to a stored value. This enables reaching a conclusion as to the condition of the person based on the measure of psychophysical perception.

In one embodiment, the stored value is based on at least one historical determination of the at least one measure of psychophysical perception of the person. This may be particularly useful in analyzing a development of a condition of the person. For instance, a person undergoing a chemotherapy treatment may be subject to demyelinization of nerve fibers. Hence, by comparing the at least one measure of psychophysical perception to historical values of the person, degeneration of the nerve fibers may be monitored.

In another embodiment, the stored value is based on determinations of the at least one measure of psychophysical perception of a plurality of persons representing a population. This implies that the measure of psychophysical perception may be compared to typical values of a population. Hence, the method may enable a conclusion to be drawn regarding the condition of the person. For instance, if the person suffers from neuropathy, which may e.g. be due to diabetes mellitus, such a condition may be identified.

In yet another embodiment, the method further comprises providing medication to the person and wherein the at least one measure of psychophysical perception is determined before and after said providing of medication. This implies that a possible difference in the at least one measure of psychophysical perception before and after providing the medication may be determined. This may be very useful, e.g. in development of new anaesthetic medications.

In a particular embodiment, the method further comprises determining an effect on a biophysical parameter by means of the medication. The difference in the at least one measure of psychophysical perception may be used for establishing an effect the medication may have on a biophysical parameter. This may be helpful in understanding how the medication affects the nervous system.

According to an embodiment of the control unit, the control unit further comprises a memory storing rules for causing a sequence of stimulation current pulses and wherein the processing unit is further arranged to determine a stimulation current strength to be used in a next stimulation current pulse based on said received signal from the interaction element and said rules for causing a sequence. The control unit may thus ensure that a sequence of stimulation current pulses is produced so that the threshold values may be accurately determined.

A method according to the invention may also or alternatively be defined as a method for assessment of nerve fiber excitability, said method comprising: arranging an electrode in contact with skin of a person; determining a first threshold value based on a stimulation current pulse of a first waveform, wherein said determining of the first threshold value comprises: repeatedly providing a stimulation current pulse of the first waveform through the electrode, wherein a stimulation current strength of the stimulation current pulse is altered between repetitions; receiving signals from an interaction element with which the person interacts, said signals from the interaction element providing an indication of the first threshold value of a stimulation current strength of the stimulation current pulse, the first threshold value corresponding to a stimulation current strength necessary to trigger a sufficiently large nerve fiber excitation such that it is perceived by the person; and determining a second threshold value based on a stimulation current pulse of a second waveform different from said first waveform, wherein said determining of the second threshold value comprises: repeatedly providing a stimulation current pulse of the second waveform through the electrode, wherein a stimulation current strength of the stimulation current pulse is altered between repetitions; receiving signals from an interaction element with which the person interacts, said signals from the interaction element providing an indication of the second threshold value of a stimulation current strength of the stimulation current pulse, the second threshold value corresponding to a stimulation current strength necessary to trigger a sufficiently large nerve fiber excitation such that it is perceived by the person; and determining at least one measure of psychophysical perception based on the determined first and second threshold values.

BRIEF DESCRIPTION OF DRAWINGS

These and other aspects of the present invention will now be described in further detail, with reference to the appended drawings showing embodiment(s) of the invention.

FIG. 3 is a flowchart of a method according to an embodiment of the invention.

FIG. 4a is a schematic view of a first stimulation current pulse having a first waveform.

FIG. 4b is a schematic view indicating a response to the first stimulation current pulse.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
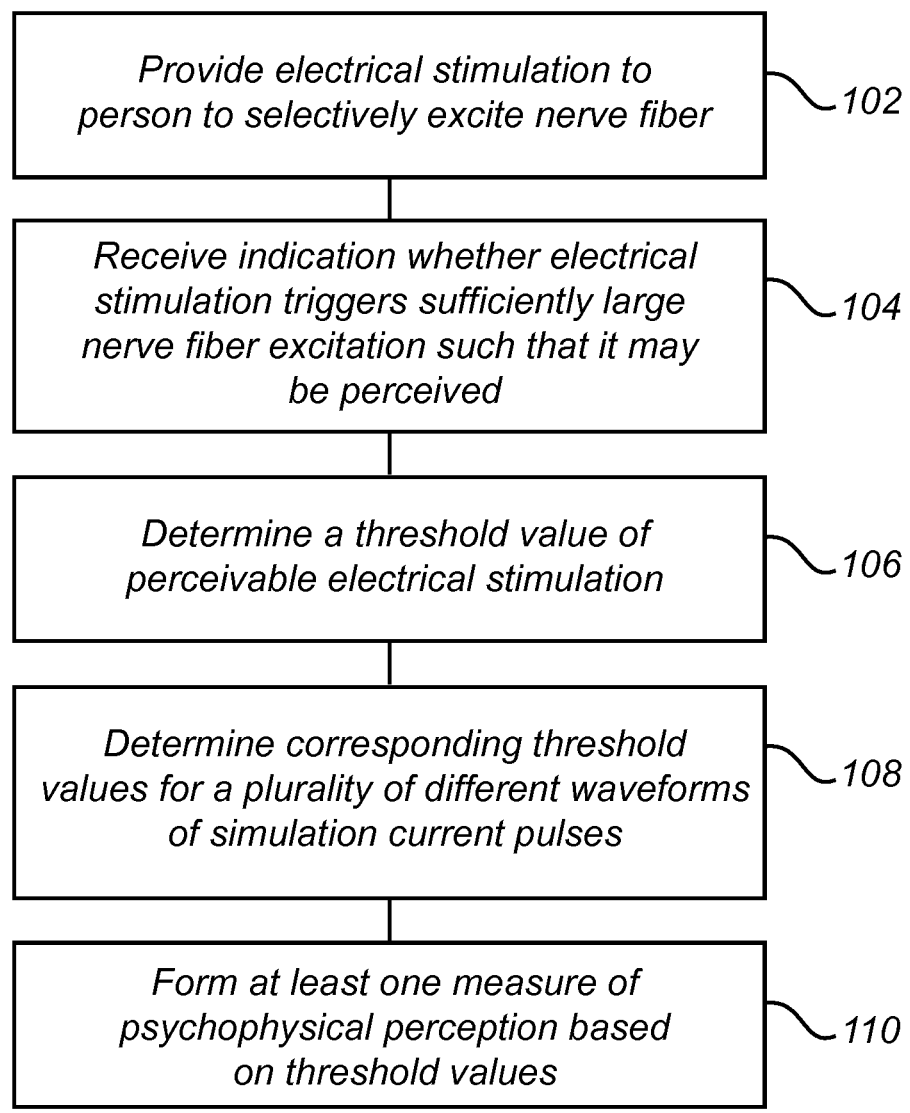
FIG. 1 is a flowchart providing a general overview of a methodology according to an embodiment of the invention.

Referring now to FIG. 1, a general overview of a methodology for measuring parameters that may be used for the determination of nerve fiber excitability of a person will be described. The methodology includes providing an electrical stimulation to the person, step 102, in order to selectively excite nerve fibers of the person. The person gives an indication whether the electrical stimulation triggers a sufficiently large nerve fiber excitation such that it may be perceived, step 104. Based on input from the person, a threshold value of perceivable electrical stimulation may be determined, step 106. Measurements of response of the person may be performed for a plurality of different waveforms of stimulation current pulses and corresponding perception-based threshold values may be determined, step 108. The perception-based threshold values may then be used for forming at least one measure of psychophysical perception, step 110.

The at least one measure of psychophysical perception may give an insight to nerve fiber functionality of the person. This may be used in several different respects. The measure of psychophysical perception may be used as input for establishing a diagnosis of a condition of the person, such as a state of nerve fiber degeneration due to e.g.

chemotherapy treatment or diabetes mellitus. The measure of psychophysical perception may also or alternatively be used for evaluating an effect of a medical substance on nerve fibers of a person.

Figure 2:
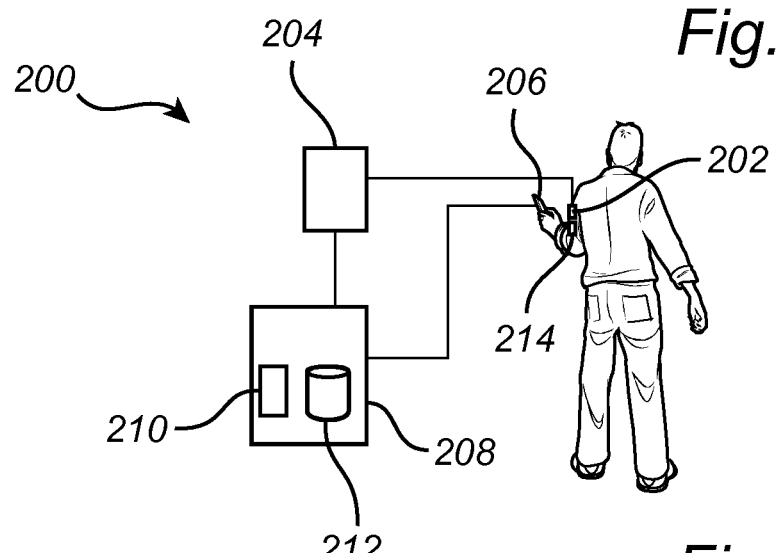
FIG. 2 is a schematical overview of a system according to an embodiment of the invention.

Referring now to FIG. 2, a system 200 for providing electrical stimulation to a person and, based on received responses, determining at least one measure of psychophysical perception of the person will be described. The system 200 comprises an electrode 202 that is to be arranged in contact with skin of the person. The electrode 202 is a surface electrode, which is arranged to make contact with the skin but not to penetrate the skin. The electrode 202 comprises at least one anode and a cathode. The anode and the cathode may be arranged in a single unit, such that only a single unit needs to be placed in contact with skin of the person. The anode and the cathode may also be designed on the single unit electrode 202 such that, when the electrode 202 is applied in contact with the skin of the person, the anode and the cathode are properly arranged in relation to each other on the person's skin. As an alternative, the electrode 202 may comprise two or more physical units carrying a cathode and an anode, respectively. In one embodiment, several physical units carrying separate cathodes may be used.

The electrode may be connected by an electrically conducting wire to a current pulse generator 204. The current pulse generator 204 may be arranged to generate and transmit a current pulse to the electrode 202 causing a current between the anode and the cathode of the electrode 202. This electrical current will be, at least partly, conducted through the skin of the person and along the superficial part of the person's skin. The electrical current may activate cutaneous nerve fibers of the person and, thus, an electrical stimulation of nerve fibers may be caused.

The electrode 202 may be designed so that the electrical current generated through the skin of the person may selectively excite different types of nerve fibers.

In one embodiment, the electrode 202 comprises a relatively large cathode area and a surrounding anode area. The total electrode area may be at least 10 mm$^2$ large. An electrode 202 having a relatively large area may excite large, afferent nerve fibers, which mainly contribute to the tactile part of the nervous system. Hence, using such an electrode 202, the Aβ-fibers may be excited and, therefore, the nerve fiber excitability of the Aβ-fibers may be analyzed.

In one embodiment, the electrode patch has an electrode area in the range of 10-250 mm$^2$, providing a sufficiently large area to excite the Aβ-fibers, while being sufficiently small to not be impractical to arrange in contact with skin of the person. In an embodiment, the electrode patch has an electrode area in the range of 50-200 mm$^2$. For instance, the electrode 202 may be circular with a diameter of 1 cm.

In another embodiment, the electrode 202 comprises a plurality of small cathodes. The cathodes may have an area of less than 5 mm$^2$. In an embodiment, the cathodes have an area in the range of 0.1-5 mm$^2$. In another embodiment, the cathodes have an area in the range of 0.2-1 mm$^2$. Further, the plurality of small cathodes may be arranged in an area smaller than 1 cm$^2$. The cathodes may form an array and may be surrounded by an annular anode. When a current pulse is provided to the electrode 202, a focused current is provided in a small area of the skin of the person. Hence, the electrode 202 will be able to selectively activate small, pain sensing nerve fibers. This implies that the nociceptors, such as Aδ-fibers and C-fibers, of the person may be selectively activated.

The current pulse generator 204 may be arranged to form a desired current pulse. The current pulse generator 204 may be arranged to enable selecting of waveform, duration of the current pulse and the current strength. The current pulse generator 204 may be arranged to receive an input signal which may be converted to an analog current pulse. Alternatively, the current pulse generator 204 may have an embedded control unit for controlling the current pulse to be output.

The current pulse generator 204 may generate pulses having different waveforms. For instance, square pulses may be generated having a constant current strength during a period of time. Also, pulses having a first part with a constant current strength during a period of time and a second part with a constant current strength different from the strength of the first part during a period of time may be created. Optionally, there may be an interval between the first and the second part. Further, non-square pulses may be generated. For instance, a pulse comprising a leading edge, wherein the stimulation current is gradually increased, such as a triangular-shaped pulse, may be generated.

The current pulse generator 204 may be arranged to generate current pulses with a constant frequency, e.g. 1 Hz. The current pulse generator 204 may further alter the current strength between two current pulses, such that the current strength is increased or decreased.

The system 200 may further comprise an interaction element 206. The interaction element 206 may form an input device, such that the person being subject to electrical stimulation may provide input whether the stimulation is perceived. The interaction element 206 may thus comprise any sensor for detecting an input from the person. For instance, the interaction element 206 may comprise one or more switches or buttons, which the person may selectively press for providing a signal indicative of whether the stimulation is perceived. For instance, the interaction element 206 may comprise one button, which the person may press as long as the stimulation is perceived and release when the stimulation is no longer perceived. In another embodiment, the interaction element 206 may provide a touch-screen presenting alternatives, such that the person may touch the alternative on the touch-screen corresponding to whether the stimulation is perceived or not. The interaction element 206 may comprise any type of sensor for detecting that a person interacts with a button or switch, such as an electric circuit being opened or closed, or a light sensor being covered or uncovered.

The interaction element 206 may comprise a holder, which is suited for being held in the person's hand. The holder may comprise a button on a top surface, such that the person may activate the button with a thumb while holding the holder.

In yet another embodiment, the interaction element 206 may provide an audio sensor for recording a sound made by the person. For instance, the interaction element 206 may comprise a microphone which may be placed close to the mouth of the person, such that audio input may be made by the person.

The interaction element 206 may further be arranged to transmit a signal indicative of detected interaction. The interaction element 206 may comprise a cable for transmitting the signal. Alternatively, or additionally, the interaction element 206 may be arranged to transmit a wireless signal, such as an electromagnetic signal. In one example, a radio frequency signal, such as Bluetooth® is used. In another example, an infrared signal, such as IrDA is used.

The system 200 may further comprise a control unit 208. The control unit 208 may be arranged to receive the input signal transmitted from the interaction element 206. The control unit 208 may thus comprise a wireless receiver or may be connected by wire to the interaction element 206.

The control unit 208 may comprise a processing unit 210 for generating a control signal in order to control the current pulse generator 204 to generate the desired current pulse. The processing unit 210 may comprise any type of processor capable of performing computer instructions. For instance, the processing unit 210 may comprise a general-purpose processor, which is provided with and executes a computer program for generating the control signal. The processing unit 210 may alternatively comprise an Application-Specific Integrated Circuit (ASIC) or a Field-Programmable Gated Array (FPGA), which is specifically adapted to execute instructions for generating control signals. As a further alternative, the processing unit 210 may be a combination of hardware and software, such as an embedded processor provided with firmware instructions.

The control unit 208 may further comprise a memory 212, which may store a scheme or rules for controlling the type of current pulses to be generated. The processing unit 210 may be connected to the memory 212 such that the scheme may be accessed by the processing unit 210 when a control signal is to be generated.

The processing unit 210 may use the scheme to determine a waveform that is to be generated by the current pulse generator 204. The processing unit 210 may further use the input signal from the interaction element 206 to determine the control signal.

When the input signal is indicative of the current stimulation not being perceived by the person, the processing unit 210 may determine that the current strength is to be increased. Similarly, when the input signal is indicative of the current stimulation being perceived by the person, the processing unit 210 may determine that the current strength is to be decreased.

The processing unit 210 may generate a control signal which merely carries an instruction to increase or decrease the current strength. Alternatively, the processing unit 210 may generate a control signal which describes the current pulse to be generated, i.e. the waveform, the current strength and the length of the pulse.

The control unit 208 may be connected, via a wire or a wireless connection, to the current pulse generator 204 for providing the control signal as input to the current pulse generator 204. The control unit 208 may alternatively be embedded in the current pulse generator 204, e.g. using an embedded processing unit in the current pulse generator 204. As a further alternative, the control unit 208 may be connected to an intermediate device, which may generate a control signal that is adapted to be received by the current pulse generator 204. For instance, the intermediate device may receive a digital control signal from the control unit 208 and convert the digital control signal to an analog control signal which may be received by the current pulse generator 204.

The control unit 208 may further comprise a computing unit, which may be a separate combination of hardware and/or software, or which may be implemented in the processing unit 210. The computing unit may be arranged to compare the current strength of the current pulses to the input signal from the interaction element 206 in order to determine threshold values for respective waveforms of the current pulse. The threshold value corresponds to a stimulation current strength necessary to trigger a sufficiently large nerve fiber excitation such that it is perceived by the person. Based on the determined threshold values, the computing unit may further be arranged to determine at least one measure of psychophysical perception, as will be further described below.

The system 200 may further comprise a temperature controller 214. The temperature controller 214 may comprise a temperature sensor, which may be arranged in contact with the person in close vicinity to the electrode 204. The temperature sensor may thus detect the temperature at the person's skin. The temperature controller 214 may be arranged to maintain the temperature as stable as possible during stimulation of the person. Thus, the temperature controller 214 may be arranged to detect changes in temperature and selectively activate a ventilator or a radiant heat source in order to control the temperature to maintain the temperature at a desired value. The temperature controller 214 may be connected to the control unit 208 for receiving a control signal, e.g. of the desired temperature value. The control unit 208 may receive the measured temperature from the temperature sensor and may provide a control signal selectively activating the ventilator or the radiant heat source. Alternatively, the temperature controller 214 may be arranged as a stand-alone unit, which may be arranged to maintain the temperature measured by the temperature sensor at a set value.

Referring now to FIG. 3, a method for providing stimulation current pulses to a person and gathering data indicative of nerve fiber excitability will be described in detail.

The method comprises arranging an electrode in contact with a person's skin, step 302. The electrode may be arranged on an extremity of the body, such as a forearm or a calf. It may be advantageous to arrange the electrode on an extremity of the body, since the longest nerve fibers extending to the extremities may be first to degenerate in neuropathy.

The method further comprises providing an electrical stimulation by generating a stimulation current pulse in the electrode, step 304. The stimulation current pulse may activate a nerve fiber of the person, such that the stimulation current pulse may be perceived by the person. The person interacts with an interaction element, such that the interaction element may generate a signal indicative of whether the stimulation current pulse is perceived or not by the person, step 306.

The stimulation current pulses may be given with an interval, such that an interaction from the person may be associated to a stimulation current pulse. In one embodiment, the stimulation current pulses may be given with an inter stimulus interval of 1 s.

The stimulation current strength may be increased until the person indicates that the stimulation current pulse is perceived, e.g. by pressing or releasing a button of the interaction element. The stimulation current strength may then be decreased until the person indicates that the stimulation current pulse is no longer perceived. The increase and decrease of the stimulation current strength may be repeated in a number of iterations in order to determine a threshold value of the stimulation current strength, step 308.

The size of the difference between two subsequent stimulation current pulses may be altered between the iterations. For instance, the size of the difference may be decreased, such that a fine-tuning of the determination of the threshold value may be performed. In one embodiment, the size of the difference is 15%, 7.5%, 7.5%, 3% and 3% in five iterations.

The stimulation current strength may continue to be increased after the person indicates that the stimulation current pulse may be perceived. The stimulation current strength may be increased to a strength that is 20%-50% above the stimulation current strength that the person indicates may be perceived. Then, the stimulation current strength is decreased again. This implies that information regarding the threshold value may be obtained both with regard to an increasing stimulation current strength and a decreasing stimulation current strength.

The threshold value may be determined as a weighted or unweighted average current strength at which the person has interacted with the interaction element to indicate that he or she starts or ceases to feel the stimulation.

The threshold value may be determined in another manner, e.g. by providing a two-alternative forced-choice task which may be synchronized with the stimulation current pulses. For instance, a screen may be arranged to display two boxes and may lit one of the boxes simultaneously with the providing of the stimulation current pulse. The person is then forced to choose which of the boxes was lit in synchronization with the stimulation current pulse. The stimulation current pulse may then be increased if the answer is incorrect and decreased if the answer is correct. Using a sequence of stimulation current pulses, a threshold value may be determined.

Referring now to FIGS. 4-7, the stimulation current pulses that may be used for determining perception-based threshold values will be further described. Several different waveforms of the stimulation current pulses may be used and the corresponding threshold values may be determined, as described above. Hence, the threshold value may be determined for a first type of waveform and, when the threshold value has been determined, a second type of waveform is used and another threshold value is determined. Thus, the control unit 208 may be arranged to control a sequence of different types of waveforms to be used in a stimulation protocol. Also, as further described below, two or more threshold values may be determined for the same type of waveform, where a parameter of the waveform is changed, such as a defined length of time of the current pulse.

As shown in FIG. 4a, the stimulation current pulse may be a square wave having a constant stimulation current strength during a defined length of time. The stimulation current pulse may have a duration in the interval of 10 μs to 50 ms.

The length of time of the stimulation current pulse is held constant, while a perception-based threshold value of the stimulation current strength is determined. Then, another defined length of time of the stimulation current pulse is used and another perception-based threshold value is determined. Hence, at least two perception-based threshold values for different defined lengths of time of the stimulation current pulse are determined.

Thus, duration-dependent threshold values may be determined. These form a strength-duration (SD) relation. The SD relation may be described by a time constant ($\tau$) describing the decrease and a rheobase ($I_r$) describing the threshold of an infinitely long pulse. FIG. 4b indicates the SD relation and the definition of the time constant and rheobase. Weiss' law defines the threshold value $I_t$ in relation to the duration of the stimulation current pulse t:

$$I_t = I_r(t+\tau).$$

Using Weiss' law, $\tau$ and $I_r$ may be calculated using only two square pulses of different durations. In one embodiment, a first defined length of time is 1 ms and a second defined length of time is 100 μs, and threshold values $T_{1\ ms}$ and $T_{100\ \mu s}$ are determined, respectively. Then, $\tau$ and $I_r$ are given by:

$$\tau = \frac{100\ \mu s \times 1\ ms \times (T_{100\ \mu s} - T_{1\ ms})}{1\ ms \times T_{1\ ms} - 100\ \mu s \times T_{100\ \mu s}}$$

and $$I_r = \frac{100\ \mu s \times T_{100\ \mu s}}{100\ \mu s + \tau}.$$

The SD data provides information about the passive properties of the nodal membrane and the voltage gated sodium channels in the nodal membrane. Thus, any pathology affecting the nodal membrane may be detected by the SD relation.

Figure 5A:
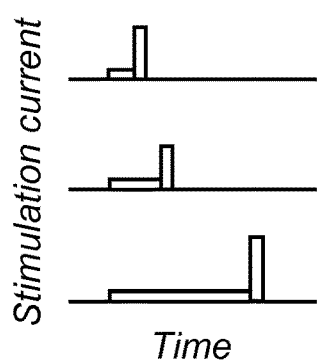
FIG. 5a is a schematic view of a second stimulation current pulse having a second waveform.

As shown in FIG. 5a, the stimulation current pulse may comprise a conditioning pulse with a strength insufficient of activation of nerve fibers and an immediately following stimulation current pulse.

The conditioning pulse may be a square pulse with a duration between 1 and 100 ms. The current strength of the conditioning pulse is below the threshold for causing a stimulation that the person may perceive. The conditioning pulse may create an electrotonic potential in nerve fibers. The electrotonic potential represents changes to the neuron's membrane potential that do not lead to the generation of new current by action potentials. Below, the stimulation current pulse comprising a conditioning pulse with an immediately following stimulation current pulse is therefore called a threshold electrotonus (TE) pulse.

In one embodiment, the current strength of the conditioning pulse may be determined based on a preceding threshold determination for gathering of SD data. The conditioning pulse need not have the same defined length of time as used in gathering SD data, since the SD relation may be used to determine the threshold value of the stimulation current strength for the defined length of time to be used in the conditioning pulse. Also, if a relatively long conditioning pulse is used, the conditioning pulse may be related to the rheobase value.

The conditioning pulse may be depolarizing or hyperpolarizing, i.e. of the same polarity or different polarity as the following stimulation current pulse. A depolarizing conditioning pulse causes a reduction of the threshold value of the following stimulation current pulse, whereas a hyperpolarizing conditioning pulse causes an increase (or negative reduction) of the threshold value of the following stimulation current pulse.

Figure 5B:
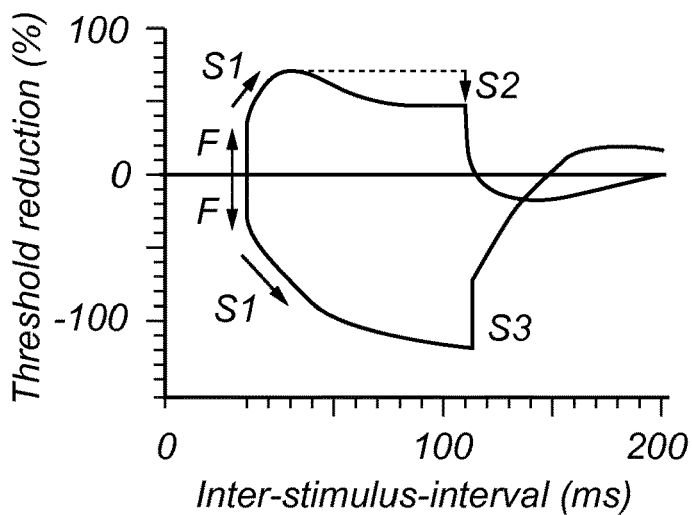
FIG. 5b is a schematic view indicating a response to the second stimulation current pulse.

A plurality of different TE pulses may be used and the perception-based threshold value may be determined for each of the TE pulses. As shown in FIG. 5b, the depolarizing and hyperpolarizing conditioning pulse cause a fast (indicated by arrow F) and a slower change (indicated by arrow S1) in the threshold value due to potential differences across the internodal membrane potential. After about 20 ms, a phase (indicated by arrow S2) is started, wherein activation of slow potassium ion channels pushes the threshold value closer to its normal value for a depolarizing conditioning pulse. The negative reduction of the threshold value by the hyperpolarizing conditioning pulse is counteracted by a slower mechanism (indicated by arrow S3) generated by activation of axonal inward rectifying channels.

The current strength of the conditioning pulse may be in the interval of ±20% to ±40% of a threshold value determined in gathering SD data. For instance, the conditioning pulse may be ±20% of the threshold value determined for a 1 ms square wave pulse in the gathering of SD data.

In one embodiment, three different TE pulses are used and the corresponding perception-based threshold values are determined for each of the TE pulses. A first TE pulse may comprise a 20 ms long depolarizing conditioning pulse and a 1 ms long following stimulation current pulse. A second TE pulse may comprise a 80 ms long depolarizing conditioning pulse and a 1 ms long following stimulation current pulse. A third TE pulse may comprise a 80 ms long hyperpolarizing conditioning pulse and a 1 ms long following stimulation current pulse.

The following stimulation current pulse used in the TE pulse may have an equally long duration as one of the stimulation current pulses used in gathering SD data. This implies that the reduction in stimulation current strength of the TE pulse may be compared to the stimulation current pulse used in the gathering of SD data.

Figure 6A:
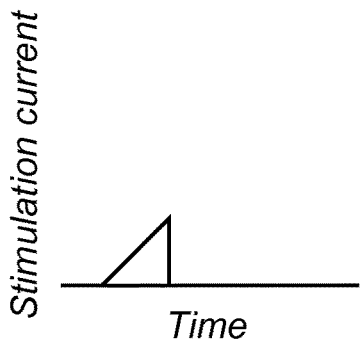
FIG. 6a is a schematic view of a third stimulation current pulse having a third waveform.

According to another embodiment, the stimulation current pulse may comprise a leading edge, wherein the stimulation current is gradually increased to the stimulation current strength. The stimulation current pulse may thus be a non-square pulse. In one embodiment, as shown in FIG. 6a, the stimulation current pulse may form a triangular waveform.

Nerve fibers may accommodate to slowly raising electrical stimulations. Therefore, in the following, the stimulation current pulse having a gradually increasing stimulation current strength is called an accommodation curve.

Figure 6B:
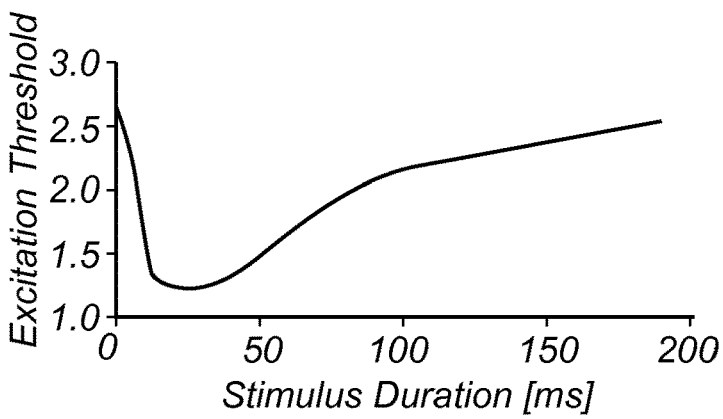
FIG. 6b is a schematic view indicating a response to the third stimulation current pulse.

As shown in FIG. 6b, when the duration of the accommodation curve is increased a decrease in activation threshold is initially observed. This decrease is similar to the SD relation observed for square wave pulses. However, if the stimulation duration is longer than approximately 20 ms the threshold value increases, due to the accommodation of the nerve fiber.

Accommodation of the nerve fibers may be related to a proportion of persistent sodium channels in nodes of the nerve fibers. For small cutaneous nerve fibers, Aδ-fibers, accommodation may not occur, which may be due to the small fibers having a large proportion of persistent sodium channels.

The accommodation curve may have a duration in the interval of 20 ms to 200 ms. Also, a plurality of accommodation curves with different durations may be used in order to determine the relation between different durations and the threshold value. In one embodiment, an accommodation curve having a duration of 20 ms is used and the corresponding threshold value is determined.

Figure 7:
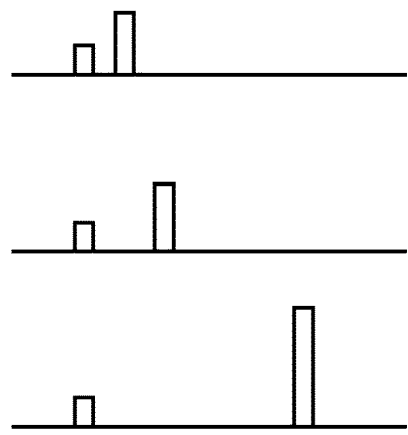
FIG. 7 is a schematic view of a fourth stimulation current pulse having a fourth waveform.

Referring now to FIG. 7, the stimulation current pulse may comprise a conditioning pulse and a following stimulation current pulse, with a delay or time interval between the conditioning pulse and the following stimulation current pulse.

The conditioning pulse adds to the neural excitability and, therefore, the activation threshold of the following stimulation current pulse is decreased. Therefore, this type of waveform will be referred to below as latent addition.

The conditioning pulse may be a square pulse having a duration in the interval of 10 μs to 10 ms. The time interval between the conditioning pulse and the following stimulation current pulse may be in the interval of 10 μs to 10 ms. The following stimulation current pulse may be a square pulse having a duration in the interval of 10 μs to 50 ms. In an embodiment, the following stimulation current pulse of the latent addition pulse has an equal length to a stimulation current pulse used in gathering SD data, which implies that a threshold change due to the conditioning pulse may be observed.

The current strength of the conditioning pulse is below the threshold for causing a stimulation that the person may perceive. The current strength of the conditioning pulse may be in the interval of 20% to 40% of a threshold value determined in gathering SD data. In one embodiment, the conditioning pulse may have a duration of 100 μs and may have a current strength that is 40% of the threshold value determined for a 100 μs square wave pulse in the gathering of SD data. The time interval between the conditioning pulse and the following stimulation current pulse may be varied between 10 μs and 500 μs and at least two different time intervals may be used. The following stimulation current pulse may have a duration of 100 μs, and a reduction in the threshold value may be determined for each of the at least two time intervals used.

Latent addition pulses may provide information of passive properties of the nodal membrane and properties of the voltage gated sodium channels in the nodal membrane.

The person is subject to at least two of the above-described waveforms and corresponding threshold values are determined for each of the waveforms in order to gather data regarding to psychophysical perception of the person.

Any combination of the different types of waveforms may be contemplated, and a plurality of waveforms, such as three or more, may be used. It should also be realized that other types of waveforms may be used in order to gather information about nerve fiber excitability using different stimulation current pulses.

In an embodiment, square wave pulses of two different defined lengths of time are used in order to gather SD data, two depolarizing TE pulses having different defined lengths of time of the conditioning pulse are used, one hyperpolarizing TE pulse is used, and one accommodation curve is used.

Although it is described above that different waveforms are sequentially used for determining threshold values associated with the respective waveforms, it should be realized that the different waveforms may be used in an interleaved procedure.

As described above, the increase and decrease of the stimulation current strength may be repeated in a number of iterations. However, these iterations need not necessarily be performed in sequence. On the contrary, using an interleaved procedure, a first iteration using a stimulation current pulse of a first waveform may be followed by a first iteration using a stimulation current pulse of a second waveform, before a second iteration using the stimulation current pulse of the first waveform is performed. Iterations of stimulation current pulses of a plurality of waveforms, such as two, three or more different waveforms, may be provided in an interleaved procedure.

Where a stimulation current pulse of one waveform is partly dependent on the threshold value of another waveform, such as a conditioning pulse being based on a threshold value determined in gathering of SD data, sufficient number of iterations of the first waveform, such as the square waveform used in gathering of SD data, may first be provided before a first iteration of the dependent waveform is provided. For instance, two iterations of square pulses for gathering SD data may be provided before the first iteration of a TE pulse is provided.

Also, the dependent waveform may be dynamically updated between iterations, such that if the threshold value of the first waveform, e.g. based on the SD data, changes, the dependent waveform, e.g. the current strength of a conditioning pulse, may be similarly changed.

Interleaving of iterations of stimulation current pulses of different waveforms may imply that a plurality of threshold values for different waveforms may be concurrently determined.

This implies that if the nerve fiber excitability of a person is affected by means of the ongoing electrical stimulations or other external factors such as temperature, the effect may be similarly reflected in all threshold values (compared to a method where the threshold values for different waveforms are determined sequentially). On the other hand, if characteristics of the dependent waveform are drastically changed during a dynamic update, more iterations may be needed in order to determine the threshold values compared to providing the different waveforms sequentially.

The control unit 208 may thus be arranged to control the current pulse generator 204 to generate the current pulses in interleaved iterations. The computing unit of the control unit 204 may be arranged to compare the current strength of the current pulses to the input signal from the interaction element 206 in order to determine threshold values for respective waveforms of the current pulse. The computing unit may determine intermediate threshold values based on one or more iterations of a waveform, such that the intermediate threshold value may be used as input for determining the current strength to be used in an iteration for another waveform. The control unit 208 may further control an order of iterations and which waveform that is to be used in each iteration.

Referring again to FIG. 3, the threshold values determined as described above may be used in order to determine at least one measure of psychophysical perception, step 310.

The threshold values provide information relating to different properties of the nerve fibers. The determined threshold values could be combined in different manners in order to provide measures of psychophysical perception. In some embodiments, such measures may be used as biomarkers for detecting whether a person suffers from some sort of neuropathy.

For instance, the determined thresholds in the gathering of SD data may be used to determine the time constant $\tau$ and the rheobase $I_r$, which both may form measures of psychophysical perception.

Further, a threshold value determined for one type of waveform may be related to a threshold value determined for another type of waveform in order to give a measure. For instance, the threshold values determined using TE pulses, accommodation curves, or latent addition pulses may be compared to threshold value(s) determined in the gathering of SD data or threshold values determined for waveforms interleaved into the iterations of stimulation current pulses. Hence, a relative reduction or increase of the threshold value for the TE pulse, accommodation curve, and latent addition pulse, respectively, may be obtained. Such a relative reduction may be used as a measure of psychophysical perception and provides a normalization of the threshold value to the person's threshold for a square pulse.

It should be realized that any linear or non-linear combination of the threshold values may be used and that such a combination may provide a measure of psychophysical perception of the person.

In one embodiment, a mathematical model of the nerve fibers may be set up, and the threshold values may be provided as input parameters to such a mathematical model, e.g. a Hodgkin-Huxley like model. The mathematical model may then provide output describing membrane properties of the nerve fibers. For instance, the membrane properties may include passive electrical properties of the nerve membrane, kinematics and distribution of ion channels (especially sodium and potassium ion channels), and ion pumps.

The computing unit may comprise instructions for calculating the at least one measure of psychophysical perception in accordance with any of the combinations of threshold values described above. The computing unit may thus output the at least one measure of psychophysical perception allowing a physician to further analyze the condition of the person.

The determined measure of psychophysical perception may be used in a variety of situations.

In one embodiment, the at least one measure of psychophysical perception is used as a biomarker, such that a physician may diagnose a condition of the person based at least partly on the at least one measure of psychophysical perception. The at least one measure may for instance be used for diagnosing neuropathy, which may e.g. be due to postherpetic neuralgia, impaired glucose intolerance, connective tissue disease, and diabetes mellitus. The at least one measure may also be used for diagnosing other disorders in the peripheral nervous system.

The computing unit may have access to a database comprising stored values of the at least one measure of psychophysical perception for a plurality of persons representing a population. The database of stored values may comprise information about the population, such as gender, age, and ethnicity. The at least one measure of psychophysical perception determined for the person may be compared by the computing unit to one or more normal values. The normal values may be based on a part of the population corresponding to a group of people to which the person belongs. The computing unit may perform the comparison of the psychophysical perception to the normal value to determine whether the measure of psychophysical perception of the person is aberrant, e.g. if the measure deviates from a standard deviation of the measure in the population. The computing unit may then output an indication whether the measure of psychophysical perception of the person is aberrant.

The at least one measure of psychophysical perception of the person may be stored into the database together with basic information about the person, such as gender, age, and any disease information, in order to successively improve the database by obtaining results from more people.

In another embodiment, the at least one measure of psychophysical perception is used for following progress of a condition of a person. For instance, chemotherapy may cause degeneration of nerve fibers and therefore lead to neuropathy. A person undergoing chemotherapy treatment may thus regularly be tested, such that a development of the at least one measure of psychophysical perception may be followed.

The at least one measure of psychophysical perception may be stored into a database of historical values with information about which person the stored value pertains to. Thus, when a new measure of psychophysical perception is determined, the measure may be compared to historical values in order to provide information of the progress. For instance, the measure of psychophysical perception may be compared to a first value and/or to a latest value.

The computing unit may have access to a database comprising stored values of the at least one measure of psychophysical perception for the person. The at least one measure of psychophysical perception determined for the person may be compared by the computing unit to one or more of the historical values. The computing unit may perform the comparison of the psychophysical perception to the historical value to determine whether the difference in the measure of psychophysical perception of the person is larger than a standard deviation for measurements. The computing unit may then output an indication that the measure of psychophysical perception of the person shows a degeneration of nerve fibers.

In yet another embodiment, the at least one measure of psychophysical perception may be used in evaluation of a medical substance. The effect of the medical substance on the nervous system may be evaluated and may provide input for the development of the medical substance.

A person, preferably a healthy person, may first be subject to electrical stimulation in order to provide a baseline measurement. The at least one measure of psychophysical perception may then be determined for the person and may be stored in a memory accessible to the computing unit. Thereafter, the person is treated by the medical substance, and after a time period allowing the substance to have effect on the person, the person is again subject to electrical stimulation. The at least one measure of psychophysical perception is determined and may be compared to the at least one measure determined pre-treatment.

Comparison of the measures of psychophysical perception may provide information about what effect the medical substance has on the nervous system. For instance, effects of the medical substance on the ion channels may be determined. In particular, if the medical substance selectively blocks a type of channel, such effect may be identified by comparing the measures of psychophysical perception before and after treatment.

The evaluation of medical substances may be useful for any type of substance that affects the nervous system, such as anaesthetic or analgesic substances, which may be provided on the skin of the person or administered to the person in any manner.

The person skilled in the art realizes that the present invention by no means is limited to the preferred embodiments described above. On the contrary, many modifications and variations are possible within the scope of the appended claims.

The invention claimed is:

1. A method for assessment of nerve fiber excitability, said method comprising:
   arranging an electrode in contact with skin of a person;
   determining a first threshold value based on a stimulation current pulse of a first waveform;
   determining a second threshold value based on a stimulation current pulse of a second waveform different from the first waveform,
   wherein said determining of the first threshold value and said determining of the second threshold value each comprises:
      repeatedly providing a stimulation current pulse of the first or second waveform, respectively, through the electrode, wherein a stimulation current strength of the stimulation current pulse is altered between repetitions; and
      receiving signals from an interaction element with which the person interacts such that the interaction element may generate a signal indicative of whether the stimulation current pulse is perceived or not by the person, said signals from the interaction element providing an indication of the first threshold value or the second threshold value, respectively, of a stimulation current strength of the stimulation current pulse, the first and second threshold value, respectively, corresponding to a stimulation current strength necessary to trigger a sufficiently large nerve fiber excitation such that it is perceived by the person; and
   determining at least one measure of psychophysical perception based on the determined first and second threshold values.

2. The method according to claim 1, further comprising determining at least a third threshold value based on a stimulation current pulse of a third waveform different from the first and second waveforms, wherein said determining of the at least third threshold value is performed in the same manner as the determining of the first and second threshold values; and wherein said determining of at least one measure of psychophysical perception is further based on the determined at least third threshold value.

3. The method according to claim 1, wherein the arranging of an electrode in contact with skin of the person comprises using an electrode patch having an electrode area larger than 10 mm$^2$ such that large myelinated, afferent nerve fibers are stimulated by the stimulation current pulse.

4. The method according to claim 1, wherein the arranging of an electrode in contact with skin of the person comprises using an array of small area electrodes having an area of less than 5 mm$^2$ such that small myelinated, afferent nerve fibers are preferentially stimulated by the stimulation current pulse.

5. The method according to claim 1, wherein the first or the second waveform is a square waveform having a constant stimulation current pulse during a defined length of time, and wherein at least two different defined lengths of time of the stimulation current pulse are used and the determining of a threshold value comprises determining a duration-dependent threshold value of the stimulation current strength for each of the defined lengths of time of the waveform.

6. The method according to claim 1, wherein the first or the second waveform comprises a conditioning pulse with a strength insufficient of activation of nerve fibers and a following stimulation current pulse.

7. The method according to claim 6, wherein the conditioning pulse depolarizes a transmembrane potential of nerve fibers.

8. The method according to claim 6, wherein the conditioning pulse hyperpolarizes a transmembrane potential of nerve fibers.

9. The method according to claim 5, wherein durations of at least two different lengths of time of the conditioning pulse with an immediately following stimulation current pulse are used, and the determining of a threshold value comprises determining a duration-dependent threshold value of the stimulation current strength for each of the defined lengths of time of the conditioning pulse.

10. The method according to claim 5, wherein durations of at least two different lengths of time between the conditioning pulse and the following stimulation current pulse are used, and the determining of a threshold value comprises determining a duration-dependent threshold value of the stimulation current strength for each of the defined lengths of time between the conditioning pulse and the following stimulation current pulse.

11. The method according to claim 1, wherein the first or the second waveform defines a pulse comprising a leading edge, wherein the stimulation current is gradually increased to the stimulation current strength.

12. The method according to claim 1, wherein said determining of the first threshold value and said determining of the second threshold value each further comprises: controlling the stimulation current strength of the stimulation current pulse based on received signals from the interaction element.

13. The method according to claim 12, wherein said controlling of the stimulation current strength comprises changing the stimulation current strength up and down around a threshold value in a plurality of iterations, wherein the determining of a threshold value is based on the plurality of iterations.

14. The method according to claim 13, wherein a size of difference in stimulation current strength between repetitions of stimulation current pulses is altered between the plurality of iterations.

15. The method according to claim 1, further comprising comparing the determined at least one measure of psychophysical perception to a stored value.

16. The method according to claim 15, wherein the stored value is based on at least one historical determination of the at least one measure of psychophysical perception of the person.

17. The method according to claim 15, wherein the stored value is based on determinations of the at least one measure of psychophysical perception of a plurality of persons representing a population.

18. The method according to claim 1, further comprising providing medication to the person and wherein the at least one measure of psychophysical perception is determined before and after said providing of medication.

19. The method according to claim 18, further comprising determining an effect on a biophysical parameter by means of the medication.

20. The method according to claim, 1 wherein the interaction element forms an input device such that the person being subjected to electrical stimulation may provide input whether the stimulation is perceived.

21. A control unit for use in assessment of nerve fiber excitability,
wherein said control unit is configured to control a stimulation current strength of a stimulation current pulse in an electrode and a waveform for the stimulation current pulse, said control unit being configured to cause a first and a second stimulation sequence using a first waveform and a second waveform different from the first waveform, respectively,
wherein said control unit is arranged to receive a signal from an interaction element with which a person interacts, such that the interaction element may generate a signal indicative of whether the stimulation current pulse is perceived or not by the person, for providing an indication whether the stimulation current pulse has triggered a sufficiently large nerve fiber excitation such that it is perceived by the person, and
wherein said control unit comprises a processing unit, which is arranged to, within each of the first and the second simulation sequences:
determine whether a stimulation current strength to be used in a next stimulation current pulse is to be increased or decreased based on said received signal from the interaction element;
store an association of values of stimulation current strength to received signals from the interaction element indicating that the stimulation current pulse is perceived by the person;
determine a threshold value of the stimulation current strength based on the stored association; and
said processing unit being further arranged to determine at least one measure of psychophysical perception based on a first threshold value determined for the first simulation sequence and a second threshold value determined for the second simulation sequence.

22. The control unit according to claim 21, wherein the control unit further comprises a memory storing rules for causing a sequence of stimulation current pulses and wherein the processing unit is further arranged to determine a stimulation current strength to be used in a next stimulation current pulse based on said received signal from the interaction element and said rules for causing a sequence.

23. The control unit according to claim 22, wherein the interaction element forms an input device such that the person being subjected to electrical stimulation may provide input whether the stimulation is perceived.

24. A system for assessment of nerve fiber excitability, said system comprising:
a control unit according to claim 21;
an electrode, which is adapted to be arranged in contact with skin of a person, wherein the electrode is operatively connected to the control unit for control of a stimulation current pulse in the electrode; and
an interaction element, which is arranged to record an interaction of the person with the interaction element providing an indication whether the stimulation current pulse has triggered a sufficiently large nerve fiber excitation such that it is perceived by the person, said interaction element being further arranged to transmit a signal to the control unit based on the interaction of the person.

* * * * *

UNITED STATES PATENT AND TRADEMARK OFFICE
CERTIFICATE OF CORRECTION

PATENT NO. : 10,791,955 B2  
APPLICATION NO. : 15/558759  
DATED : October 6, 2020  
INVENTOR(S) : K. Hennings et al.

Page 1 of 1

It is certified that error appears in the above-identified patent and that said Letters Patent is hereby corrected as shown below:

| Column | Line | |
|---|---|---|
| In the Drawings | | |
| Fig. 1, Block 108 | 3 | "of simulation" to -- of stimulation -- |
| In the Specification | | |
| 2 | 66 | "simulation sequences" to -- stimulation sequences -- |
| 3 | 10 | "simulation sequence" to -- stimulation sequences -- |
| 3 | 11 | "simulation sequence" to -- stimulation sequence -- |
| In the Claims | | |
| 22 | 6 | Claim 21 "simulation sequences" to -- stimulation sequences -- |
| 22 | 21 | Claim 21 "simulation sequence" to -- stimulation sequence -- |
| 22 | 22 | Claim 21 "simulation sequence" to -- stimulation sequence -- |

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*